United States Patent [19]

Singer

[11] 4,007,033
[45] Feb. 8, 1977

[54] HERBICIDAL SUBSTITUTED-HALOETHYL UREA

[75] Inventor: Malcolm Scott Singer, Richmond, Calif.

[73] Assignee: Chevron Research Company, San Francisco, Calif.

[22] Filed: May 29, 1975

[21] Appl. No.: 581,985

Related U.S. Application Data

[60] Division of Ser. No. 389,093, Aug. 17, 1973, Pat. No. 3,903,154, which is a continuation-in-part of Ser. No. 385,521, Aug. 3, 1973, abandoned, which is a continuation-in-part of Ser. Nos. 124,422, March 16, 1971, abandoned, and Ser. No. 124,423, March 16, 1971, abandoned.

[52] U.S. Cl. .................. 71/111; 71/106; 71/119; 71/120; 260/468 J; 260/470; 260/471 A; 260/481 R; 260/482 R; 260/553 R; 260/553 A; 260/553 D
[51] Int. Cl.² .............. A01N 9/20; C07C 127/19
[58] Field of Search ............ 260/471 R; 71/111

[56] References Cited
UNITED STATES PATENTS 3,808,262 4/1974 Zeeh et al. ............ 260/471 A X
3,862,208 1/1975 Zeeh et al. ............ 260/471 A Primary Examiner—Richard L. Raymond
Attorney, Agent, or Firm—George F. Magdeburger; Dix A. Newell; Raymond Owyang

[57] ABSTRACT

Herbicidal compounds of the formula

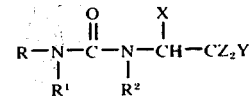

wherein R is alkyl, cycloalkyl or phenyl substituted with up to 2 fluorine, chlorine, bromine, trifluoromethyl, nitro, lower alkoxy, lower alkyl or phenoxy, phenylthio or phenylsulfonyl substituted with up to 2 fluorine or chlorine atoms; $R^1$ is hydrogen or alkyl; $R^2$ is alkyl; Z is halogen; Y is hydrogen or Z; and X is alkoxy, carbalkoxyalkoxy, alkylthio, carbalkoxyalkylthio or phenylthio substituted with up to 2 fluorine, chlorine, bromine or lower alkyl groups.

10 Claims, No Drawings

HERBICIDAL SUBSTITUTED-HALOETHYL UREA

RELATED APPLICATIONS

This application is a division of Ser. No. 389,093, filed Aug. 17, 1973, now U.S. Pat. No. 3,903,154, which is a continuation-in-part of application Ser. No. 385,521, filed Aug. 3, 1973, now abandoned, which is a continuation-in-part of application Ser. Nos. 124,422 and 124,423, both abandoned, filed Mar. 16, 1971. The disclosures of Ser. Nos. 385,521 and 124,422 are incorporated herein by reference.

DESCRIPTION OF THE PRIOR ART

U.S. Pat. No. 3,040,802 discloses β-polyhalo-α-hydrocarbyl isocyanates and derivatives thereof, such as 1-(1-hydroxy-2,2,2-trifluoroethyl)-3-phenyl urea and 1-(1-hydroxy-2,2,2-trichloroethyl)-3-phenyl urea, and their use as herbicides. Hoover et al, J. Org. Chem. 28(7), 1825-30 (1963) disclose compounds such as 1-(1-hydroxy-2,2,2-trifluoro-1-chloroethyl)-3-phenyl urea. Chattaway et al, Proc. Roy. Soc. (London) A-134, pages 372-84 (1931), and Chattaway et al, J. Chem. Soc. 1933, 30, disclose compounds prepared by the condensation of chloral with tolyl and nitrophenyl ureas. Also, U.S. Pat. Nos. 2,846,399, 2,902,356, 3,418,334 and 3,488,376 disclose ureas and their uses.

DESCRIPTION OF THE INVENTION

Compounds of the present invention may be represented by the formula (I)

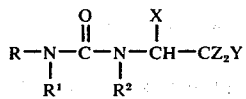

(I)

wherein R is alkyl of 1 to 12 carbon atoms, cycloalkyl of 3 to 8 carbon atoms, or phenyl substituted with up to 2 (0 to 2) fluorine, chlorine, bromine, trifluoromethyl, nitro, lower alkoxy, lower alkyl, or phenoxy, phenylthio or phenylsulfonyl substituted with up to 2 fluorine or chlorine; $R^1$ is hydrogen or alkyl of 1 to 4 carbon atoms; $R^2$ is alkyl of 1 to 4 carbon atoms; Z is chlorine or bromine; Y is hydrogen or Z; and X is alkoxy of 1 to 6 carbon atoms, alkylthio of 1 to 6 carbon atoms, carbalkoxyalkoxy of 2 to 6 carbon atoms, carbalkoxyalkylthio of 2 to 6 carbon atoms or phenylthio substituted with up to 2 fluorine, chlorine, bromine or lower alkyl groups.

Preferably R is alkyl of 1 to 6 carbon atoms, cycloalkyl of 5 to 6 carbon atoms or phenyl substituted with 1 to 2 fluorine, chlorine, bromine, trifluoromethyl, lower alkoxy or lower alkyl groups. More preferably, R is phenyl substituted with 1 to 2 fluorine or chlorine. A single trifluoromethyl or fluorine group is preferably attached to the phenyl in the ortho position. Preferably Y is chlorine or bromine, $R^1$ is hydrogen and $R^2$ is alkyl of 1 to 4 carbon atoms. More preferably $R^2$ is methyl.

Representative groups which R may represent include methyl, ethyl, n-propyl, isopropyl, n-butyl, isobutyl, sec.butyl, decyl, dodecyl, cyclopropyl, cyclobutyl, cyclopentyl, cyclohexyl, phenyl, 2-fluorophenyl, 2-chlorophenyl, 2-chloro-4-bromophenyl, 3-methylphenyl, 4-methoxyphenyl, 2-nitrophenyl, 2-trifluoromethylphenyl, 4-phenoxyphenyl, 4-phenylthiophenyl, 4-phenylsulfonylphenyl, and 4-(2-chlorophenoxy)phenyl.

Representative groups which $R^1$ may represent include hydrogen, methyl, ethyl, n-propyl, isopropyl, etc.

Representative groups which $R^2$ may represent include methyl, ethyl, n-propyl, isopropyl, n-butyl, isobutyl, etc.

Representative alkylthio X groups include methylthio, ethylthio, isopropylthio, n-butylthio, and n-hexylthio. Representative alkoxy X groups include methoxy, isopropoxy and hexoxy. Representative carbalkoxyalkoxy X groups include carbomethoxymethoxy, carbomethoxyethoxy, carbobutoxymethoxy, and carbomethoxypropoxy. Representative carbalkoxyalkylthio X groups include carbomethoxymethylthio, carbomethoxyethylthio and carbopropoxymethylthio. Representative substituted-phenylthio X groups include p-chlorophenylthio, 3,4-dichlorophenylthio and p-tolylthio.

Representative compounds of the invention include:
1-methyl-1-(1-methylthio-2,2,2-trichloroethyl)-3-(4-phenoxyphenyl) urea,
1-methyl-1-(1-ethylthio-2,2,2-trichloroethyl)-3-(4-[4'-chlorophenoxy]phenyl urea,
1-ethyl-1-(1-methoxy-2,2,2-tribromomethyl)-3-(4-phenylsulfonylphenyl) urea,
1-methyl-1-(1-ethylthio-2,2,2-trichloroethyl)-3-(4-phenylthiophenyl) urea,
1-methyl-1-(1-methoxy-2,2,2-trichloroethyl)-3-(2-fluorophenyl) urea,
1-methyl-1-(1-ethoxy-2,2,2-tribromoethyl)-3-(2-chlorophenyl) urea,
1-methyl-1-(1-methylthio-2,2,2-trichloroethyl)-3-(4-nitrophenyl) urea,
1-methyl-1-(1-isopropylthio-2-bromo-2,2-dichloroethyl)-3-(3-chloro-4-methoxyphenyl) urea,
1-methyl-1-(1-carbomethoxymethylthio-2,2,2-trichloroethyl)-3-(2-fluorophenyl) urea,
1-methyl-1-(1-carbethoxymethylthio-2-bromo-2,2-dichloroethyl)-3-(3-chlorophenyl) urea,
1-methyl-1-(1-carbomethoxymethoxy-2,2-dichloroethyl)-3-(2,4-dichlorophenyl) urea, 1-methyl-1-(1-p-chlorophenylthio-2,2,2-trichloroethyl)-3-(2-nitrophenyl) urea, and
1-ethyl-1-(1-p-tolylthio-2,2,2-trichloroethyl)-3-(2-methyl-4-chlorophenyl) urea.

The preferred compounds of the invention are those wherein R, $R^1$, $R^2$, Y and Z are as defined above and Y is alkylthio, especially alkylthio of 1 to 3 carbon atoms.

The compounds of the present invention are prepared from α-hydroxy compounds represented by formula (IV). Such compounds are prepared by reacting a urea with an aldehyde according to the following equation (1)

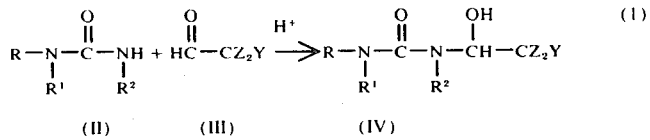

wherein R, R¹, R², Y and Z are as defined above.

The urea reactants (II) employed for reaction (1) are known compounds of the prior art. The aldehyde may be a compound such as chloral (trichloroacetaldehyde), dichloroacetaldehyde, dichlorobromoacetaldehyde, tribromoacetaldehyde, etc. Reaction (1) may be accomplished in the presence of a solvent or neat. Generally, stoichiometric amounts of the urea and aldehyde will be used. A small amount of acid, preferably sulfuric acid or perchloric acid, may be used. The reaction temperature will be from 20° to 100° C. Generally the reaction proceeds very rapidly and will be complete in a matter of a few minutes. Reaction times of from 30 seconds to 10 hours are considered sufficient.

The α-hydroxy compound (IV) is converted to the α-chloro compound represented by formula (V) by reacting the α-hydroxy compound (IV) either in purified form or in the reaction mixture of reaction (1) with thionyl chloride according to the following equation (2):

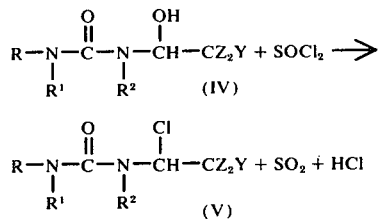

wherein R, R¹, R², Y and Z are as defined above.

The reaction (2) can be accomplished by using from a molar amount of thionyl chloride to an excess of as much as 20 mols, based on the urea. The reaction temperature will be from 20° to 100° C. and reaction time will be from 1 to 20 hours. If desired, reactions (1) and (2) may be combined to prepare the α-chloro compound (V) by simply mixing together the urea reactant (II), the aldehyde reactant (III) and the thionyl chloride. The α-chloro product (V) can be recovered by slurrying in a solvent such as diethyl ether or methylene chloride, collecting the product on a filter, then properly purifying by recrystallizing from a 1:1 mixture of 1,2-dimethoxymethane and methylene chloride or from a 1:1 acetone and methylene chloride mixture.

The compounds of the present invention are prepared by reacting the α-chloro compound (V) with an alkanol (X = alkoxy), an alkyl mercaptan (X = alkylthio), a carbalkoxy-substituted alkanol or alkyl mercaptan (X = carbalkoxyalkoxy or carbalkoxyalkylthio) or a thiophenol (X = phenylthio or substituted-phenylthio), as shown in reaction (3) below:

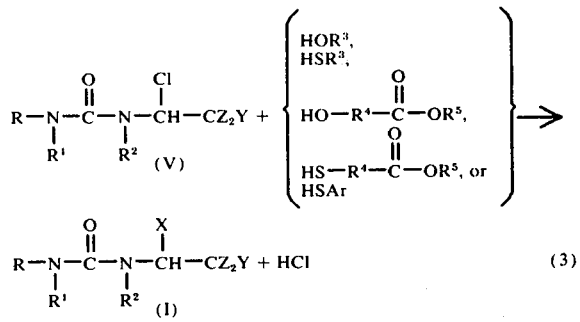

wherein R, R¹, R², Z and X are as defined above, and HOR³ represents an alkanol, HSR³ represents an alkyl mercaptan,

represents a carbalkoxyalkanol,

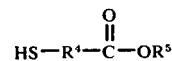

represents a carbalkoxyalkyl mercaptan, and HSAr represents a thiophenol.

The above reaction (3) can be accomplished readily by mixing the reactants preferably in a solvent such as 1,2-dimethoxyethane in an amount from 2 to 50% by volume for a time from about 0.25 to 20 hours at a temperature from about 20° to 100° C. The solvent is then removed and the product slurried in ether and collected. Generally the reactant in brackets will be in excess, in an amount of 5 to 100% of the α-chloro urea reactant (V).

The present invention will be more fully understood by reference to the following examples.

EXAMPLES

EXAMPLE 1

Preparation of
1-methyl-1-(1-hydroxy-2,2,2-trichloroethyl)-3-phenyl urea 1-methyl-3-phenyl urea (7.5 g, 0.05 mol) was reacted with 7.5 g (0.05 mol) of chloral without solvent. The mixture was shaken for a short period of time. After, three drops of perchloric acid were added and the mixture heated gently for a few minutes to give a homogenous viscous oil. Upon cooling, a glass formed. The chemical analysis showed: %Cl, calculated 35.8, found 35.8; %N, calculated 9.4, found 8.0.

EXAMPLE 2

Preparation of 1-methyl-1-(1,2,2,2-tetrachloroethyl)-3-(2-fluorophenyl) urea N-methyl-N'-o-fluorophenyl urea (16.8 g, 0.1 mol) was combined with 22.5 g (0.15 mol) chloral and 18.0 g (0.15 mol) thionyl chloride. After several minutes an exothermicity was noted and the reaction mixture became a homogenous yellow oil. After 5 minutes more, a precipitate began to form. After 1½ hours a 3:1 mixture of diethyl ether:petroleum ether was added and the product was collected on a filter and dried. The solid, which weighed 25 g, melted at 130°–141° C. and analyzed as follows: %Cl, calculated 35.7, found 37.3; %N, calculated 9.5, found 9.5.

EXAMPLE 3

Preparation of 1-methyl-1-(1,2,2,2-tetrachloroethyl)-3-(3,4-dichlorophenyl) urea 1-(3,4-dichlorophenyl)-3-methyl urea (15.2 g, 0.07 mol) was combined with 15.0 g (0.1 mol) of chloral and 5 drops of concentrated sulfuric acid. The mixture was heated for an hour to effect reaction, then stripped under vacuum. To the crude 1-(3,4-dichlorophenyl)-3-(1-hydroxy-2,2,2-trichloroethyl)-3-methyl urea was added an excess of thionyl chloride and the mixture was heated gradually to a maximum of 65° C. Diethyl ether was added to the crude product, and the insoluble product was collected on a filter, washed twice with diethyl ether and dried. The 15.3 g of product, which melted at 132°–140° C., analyzed as follows: %Cl, calculated 55.2, found 46.0.

EXAMPLE 4

Preparation of 1-methyl-1(1,2,2,2,-tetrachloroethyl)-3-(4-phenoxyphenyl) urea p-Phenoxyaniline (11.7 g, 0.063 mol) was dissolved in 25 ml. 1,2-dimethoxyethane (Ansul E-121) and heated to 65° C. Methyl isocyanate (3.7 g, 0.65 mol) was added over a period of 10 minutes. Heating and stirring were continued for 1 hour. Then chloral (14.8 g, 0.1 mol) was added to the hot solution, followed immediately by the addition of 11.9 g (0.1 mol) thionyl chloride. It was kept at 65° C. for 4½ hours. The solution was cooled to 40°, and 25 ml of methylene chloride was added. The solution was refluxed for one more hour and then allowed to cool. The solid which formed upon cooling was filtered, washed with methylene chloride to give 5.0 g (20% yield) of a white powder, melting point 165°–167° C. A second crop, melting point 160°–162° C., weighed 5.5 g (22%). Elemental analysis showed: %Cl, calc. 34.8, found 34.35; %N, calc. 6.9, found 6.8; %C, calc. 47.1, found 47.5; %H, calc. 3.46, found 3.3.

EXAMPLE 5

Preparation of 1-methyl-1-(1-methylthio-2,2,2-trichloroethyl)-3-(2-fluorophenyl) urea 1-methyl-1-(1,2,2,2-tetrachloroethyl)-3-(2-fluorophenyl) urea (16.7 g, 0.05 mol) was dissolved by heating (30°–40° C.) in 100 cc dimethoxyethane, then methylmercaptan was bubbled into the hot solution for 20 minutes. An initial exothermicity occurred, then the temperature dropped gradually to 30° C. Removal of the solvent yielded a solid, which after being slurried in ether was collected on a filter and dried. The crystalline solid, 7 g, melted at 127°–130° C. and analyzed as follows: %S, calc. 9.3, found 8.0; %Cl, calc. 30.8, found 26.9.

Other compounds and intermediates of the present invention were prepared using the methods as described above. These compounds are listed in Table I.

UTILITY

The ureas of the present invention are, in general, herbicidal in both pre- and post-emergent applications. For pre-emergent control of undesirable vegetation, these ureas will be applied in herbicidal quantities to the environment, e.g., soil infested with seeds and/or seedlings of such vegetation. Such application will inhibit the growth of or kill the seeds, germinating seeds and seedlings. For post-emergent applications, the ureas of the present invention will be applied directly to the foliage and other plant parts. Generally they are effective against weed grasses as well as broadleaved weeds. Some may be selective with respect to type of application and/or type of weed.

Pre- and post-emergent herbicidal tests on representative ureas of this invention were made using the following methods:

Pre-Emergent Test

Acetone solutions of the test ureas were prepared by mixing 750 mg urea, 220 mg of a nonionic surfactant and 25 ml of acetone. This solution was added to approximately 125 ml of water containing 156 mg of surfactant.

Seeds of the test vegetation were planted in a pot of soil and the urea solution was sprayed uniformly onto the soil surface at a dose of 100 mg per $cm^2$. The pot was watered and placed in a greenhouse. The pot was watered intermittently and was observed for seedling emergence, health of emerging seedlings, etc., for a 3-week period. At the end of this period, the herbicidal effectiveness of the urea was rated, based on the physiological observations. A 0-to-100 scale was used, 0 representing no phytotoxicity, 100 representing complete kill.

Post-Emergent Test

The test ureas were formulated in the same manner as described above for the pre-emergent test. The concentration of the urea in this formulation was 5000 ppm. This formulation was uniformly sprayed on 2 similar pots of 24-day-old plants (approximately 15 to 25 plants per pot) at a dose of 100 mg per $cm^2$. After the plants had dried, they were placed in a greenhouse and then watered intermittently at their bases, as needed. The plants were observed periodically for phytotoxic effects and physiological and morphological responses to the treatment. After 3 weeks the herbicidal effectiveness of the urea was rated, based on these observations. A 0to-100 scale was used, 0 representing no phytotoxicity, 100 representing complete kill.

The results of these tests appear in Table II.

The amount of urea administered will vary with the particular plant part or plant growth medium which is to be contacted, the general location of application — i.e., sheltered areas such as greenhouses as compared to exposed areas such as fields — as well as the desired type of control. For pre-emergent control of most plants, dosages in the range of about 0.5 to 20 lbs per acre will be used. Such administration will give a concentration of about 2 to 80 ppm urea distributed throughout 0.1 acrefoot. For post-emergent application, such as foliar spray application, compositions containing about 0.5 to 8 lbs urea per 100 gals spray will be used. Such application is equivalent to about 0.5 to 20 lbs urea per acre.

The herbicidal compositions of this invention comprise an herbicidal amount of one or more of the above-described ureas intimately admixed with a biologically inert carrier. The carrier may be a liquid diluent, such as water or acetone, or a solid. The solid may be in the form of dust powder or granules. These compositions will also usually contain adjuvants such as a wetting or dispersing agent to facilitate their penetration into the plant growth medium or plant tissue and generally enhance their effectiveness. These compositions may also contain other pesticides, stabilizers, conditioners, fillers, and the like.

TABLE I

| Compound | Halogen Calc. | Halogen Found | N Calc. | N Found | S Calc. | S Found | Melting Point ° C. |
|---|---|---|---|---|---|---|---|
| 1-methyl-1-(1-ethoxy-2,2,2-trichloroethyl)-3-(2-fluorophenyl) urea | Cl 27.2<br>F 7.3 | 27.6<br>7.2 | | | | | 162–163 |
| 1-methyl-1-(1-ethoxy-2,2,2-trichloroethyl)-3-(2-chlorophenyl) urea | 38.4 | 38.8 | | | | | 124–127 |
| 1-methyl-1-(1-ethoxy-2,2,2-trichloroethyl)-3-(2-trifluoromethylphenyl) urea | Cl 22.8<br>F 18.3 | 22.6<br>18.6 | | | | | 123–127 |
| 1-methyl-1-(1-methoxy-2,2,2-trichloroethyl)-3-(3-tolyl) urea | 32.6 | 30.5 | 8.6 | 8.2 | | | 133–135 |
| 1-methyl-1-(1-ethoxy-2,2,2-trichloroethyl)-3-(3-chlorophenyl) urea | 39.4 | 38.7 | 7.8 | 7.0 | | | 104–106 |
| 1-methyl-1-(1-methoxy-2,2,2-trichloroethyl)-3-(2-fluorophenyl) urea | 32.2 | 32.2 | 8.5 | 8.5 | | | 152–153 |
| 1-methyl-1-(1-methylthio-2,2,2-trichloroethyl)-3-(2-fluorophenyl) urea | 30.8 | 26.9 | | | 9.3 | 8.0 | 127–130 |
| 1-methyl-1-(1-ethylthio-2,2,2-trichloroethyl)-3-(2-fluorophenyl) urea | 29.5 | 29.1 | | | 8.9 | 8.4 | 144–147 |
| 1-methyl-1-(1-phenylthio-2,2,2-trichloroethyl)-3-(2-fluorophenyl) urea | 26.0 | 25.3 | | | 7.9 | 7.8 | 121–125 |
| 1-methyl-1-(1-methylthio-2,2,2-trichloroethyl)-3-(3-tolyl) urea | 31.1 | 30.6 | | | 9.4 | 9.8 | 132–134 |
| 1-methyl-1-(1-methylthio-2,2,2-trichloroethyl)-3-(3-chlorophenyl) urea | 39.2 | 38.5 | | | 8.8 | 9.1 | 127–130 |
| 1-methyl-1-(1-ethylthio-2,2,2-trichloroethyl)-3-(3-chlorophenyl) urea | 37.8 | 35.4 | | | 8.5 | 8.0 | 142–145 |
| 1-methyl-1-(1-ethylthio-2,2,2-trichloroethyl)-3-(3,4-dichlorophenyl) urea | 43.2 | 40.1 | | | 7.8 | 7.3 | 125–128 |
| 1-methyl-1-(1-methylthio-2,2,2-trichloroethyl)-3-(3,4-dichlorophenyl) urea | 44.7 | 41.4 | | | 8.1 | 7.4 | 151–153 |
| 1-methyl-1-(1-ethylthio-2,2,2-trichloroethyl)-3-phenyl urea | 31.1 | 30.4 | | | 9.4 | 7.9 | 155–157 |
| 1-methyl-1-(1-carbethoxymethylthio-2,2,2-trichloroethyl)-3-(3-chlorophenyl) urea | 32.7 | 31.7 | | | 7.4 | 7.0 | oil |
| 1-methyl-1-(1-carbethoxymethylthio-2,2,2-trichloroethyl)-3-(3,4-dichlorophenyl) urea | 37.8 | 34.9 | | | 6.8 | 6.9 | oil |
| 1-methyl-1-(1-carbethoxymethylthio-2,2,2-trichloroethyl)-3-(2-fluorophenyl) urea | 25.4 | 25.7 | | | 7.7 | 7.4 | oil |
| 1-methyl-1-(1-carbethoxymethoxy-2,2,2-trichloroethyl)-3-(3-chlorophenyl) urea | 34.0 | 30.3 | 6.7 | 6.5 | | | oil |
| 1-methyl-1-(1-carbethoxymethoxy-2,2,2-trichloroethyl)-3-(3,4-dichlorophenyl) urea | 39.2 | 36.7 | 6.2 | 5.4 | | | oil |
| 1-methyl-1-(1-carbethoxymethoxy-2,2,2-trichloroethyl)-3-(2-fluorophenyl) urea | Cl 26.4<br>F 4.7 | 26.6<br>4.8 | | | | | oil |
| 1-methyl-1-(1-methoxy-2,2,2-trichloro)-3-(3,4-dichlorophenyl) urea | | | 7.4 | 8.0 | 34.7* | 35.9* | 165–168 |
| 1-methyl-1-(1-methylthio-2,2,2-trichloroethyl)-3-cyclohexyl urea | | | 8.4 | 8.1 | | | 148–150 |
| 1-methyl-1-(1-methylthio-2,2,2-trichloroethyl)-3-methyl urea | 40.1 | 38.6 | | | 12.1 | 11.1 | 167–168 |
| 1-methyl-1-(1-methylthio-2,2,2-trichloroethyl)-3-cyclopentyl urea | 33.3 | 33.4 | | | 10.0 | 10.2 | 121–123 |
| 1-methyl-1-(1-methylthio-2,2,2-trichloroethyl)-3-t-butyl urea | 34.6 | 35.1 | | | 10.4 | 10.4 | 102–103 |
| 1-methyl-1-(1-methylthio-2,2,2-trichloroethyl)-3-dodecyl urea | 25.3 | 23.3 | | | 7.6 | 7.2 | 48–49 |
| 1-methyl-1-(1-chloro-2,2,2-tribromoethyl)-3-(3,4-dichlorophenyl urea | 11.6** | 11.6** | 5.4 | 5.5 | | | 155–158 |
| 1-methyl-1-(1,2,2,2-tetrachloroethyl)-3-(4-methoxyphenyl) urea | 41.1 | 40.1 | 8.1 | 8.2 | | | 176–179 |
| 1-methyl-1-(1,2,2-trichloro-2-bromoethyl)-3-(3,4-dichlorophenyl) urea | 14.0** | 13.8** | 6.2 | 6.3 | | | 166–169 |
| 1-methyl-1-(1,2,2-trichloro-2-bromoethyl)-3-(3-chlorophenyl) urea | Cl*** 9.0 | 8.4 | | | | | 150–152 |
| 1-methyl-1-(1,2,2,2-tetrachloroethyl)-3-(3-trifluoromethylphenyl) urea | Cl*** 9.3<br>F 14.8 | 9.2<br>14.9 | | | | | 138–142 |
| 1-methyl-1-(1,2,2,2-tetrachloroethyl)-3-[-methyl-4-(4'-chlorophenylthio)phenyl] urea | 37.5 | 35.4 | | | 6.8 | 6.8 | 152–154 |
| 1-methyl-1-(1,2,2,2-tetrachloroethyl)-3-[3-methyl-4-(4'-chlorophenylsulfonyl)phenyl] urea | 35.1 | 29.0 | | | 6.3 | 6.8 | 168–171 |
| 1-methyl-1-(1,2,2-trichloroethyl)-3-(3-chlorophenyl) urea | | | 8.9 | 8.9 | 38.0** | 38.0** | 118–127 |
| 1-methyl-1-(1,2,2,2-tetrachloroethyl)-3-[4-(4'-chlorophenoxy)phenyl] urea | 40.1 | 39.6 | 6.3 | 6.3 | | | 153–156 |
| 1-methyl-1-(1,2,2,2-tetrachloroethyl)-3-cyclopentyl urea | | | 9.1 | 8.7 | | | 132–136 |
| 1-methyl-1-(1,2,2,2-tetrachloroethyl)-3-cyclohexyl urea | | | 8.7 | 8.4 | | | 127–129.5 |
| 1-methyl-1-(1,2,2,2-tetrachloroethyl)-3-methyl urea | | | 11.0 | 10.9 | | | 73–76 |
| 1-methyl-1-(1,2,2,2-tetrachloroethyl)-3-n-hexyl urea | | | 8.7 | 9.2 | | | 45–55 |
| 1-methyl-1-(1,2,2,2-tetrachloroethyl)-3-t-butyl urea | | | 9.5 | 9.7 | 32.5* | 31.7* | 84–88 |

TABLE I-continued

| Compound | Elemental Analysis | | | | | | Melting Point °C. |
|---|---|---|---|---|---|---|---|
| | Halogen | | N | | S | | |
| | Calc. | Found | Calc. | Found | Calc. | Found | |
| 1-methyl-1-(1,2,2,2-tetrachloroethyl)-3-n-dodecyl urea | 34.7 | 33.5 | 6.9 | 6.3 | | | 39–41 |

*carbon analysis
**analysis for total halogen in milliequivalents per gram
***analysis for active halogen (i.e., the halogen on the carbon adjacent to the 1-nitrogen atom)

TABLE II

| Compound | Herbicidal Effectiveness Pre/Post | | | | | |
|---|---|---|---|---|---|---|
| | O | W | C | M | P | L |
| 1-methyl-1-(1-ethoxy-2,2,2-trichloroethyl)-3-(2-fluorophenyl) urea | 00/0 | 0/0 | 0/0 | 93/85 | 100/85 | 100/90 |
| 1-methyl-1-(1-ethoxy-2,2,2-trichloroethyl)-3-(2-trifluoromethylphenyl) urea | 30/10 | 35/0 | 35/0 | 85/100 | 80/98 | 90/60 |
| 1-methyl-1-(1-methoxy-2,2,2-trichloroethyl)-3-(3-tolyl) urea | 30/0 | 80/0 | 30/20 | 45/30 | 30/35 | 100/30 |
| 1-methyl-1-(1-ethoxy-2,2,2-trichloroethyl)-3-(3-chlorophenyl) urea | 10/40 | 20/50 | 35/40 | 55/100 | 75/95 | 75/100 |
| 1-methyl-1-(1-methoxy-2,2,2-trichloroethyl)-3-(2-fluorophenyl) urea | 55/0 | 50/0 | 90/0 | 70/60 | 85/100 | 65/95 |
| 1-methyl-1-(1-methylthio-2,2,2-trichloroethyl)-3-(2-fluorophenyl) urea | 100/100 | 100/100 | 100/95 | 100/100 | 100/100 | 100/100 |
| 1-methyl-1-(1-ethylthio-2,2,2-trichloroethyl)-3-(2-fluorophenyl) urea | 100/25 | 100/35 | 100/0 | 100/95 | 100/60 | 100/90 |
| 1-methyl-1-(1-phenylthio-2,2,2-trichloroethyl)-3-(2-fluorophenyl) urea | 100/10 | 60/20 | 85/0 | 100/95 | 100/45 | 85/75 |
| 1-methyl-1-(1-methylthio-2,2,2-trichloroethyl)-3-(3-tolyl) urea | 30/0 | 45/45 | 50/10 | 20/55 | 25/50 | 80/90 |
| 1-methyl-1-(1-methylthio-2,2,2-trichloroethyl)-3-(3-chlorophenyl) urea | 40/0 | 25/0 | 40/0 | 50/70 | 25/55 | 20/70 |
| 1-methyl-1-(1-ethylthio-2,2,2-trichloroethyl)-3-(3-chlorophenyl) urea | 10/0 | 15/0 | 0/0 | 0/70 | 50/45 | 50/55 |
| 1-methyl-1-(1-ethylthio-2,2,2-trichloroethyl)-3-(3,4-dichlorophenyl) urea | 65/100 | 94/100 | 35/90 | 10/0 | 13/0 | 0/0 |
| 1-methyl-1-(1-methylthio-2,2,2-trichloroethyl)-3-(3,4-dichlorophenyl) urea | 45/65 | 75/93 | 30/40 | 20/0 | 0/0 | 0/0 |
| 1-methyl-1-(1-ethylthio-2,2,2-trichloroethyl)-3-phenyl urea | 0/0 | 0/0 | 0/0 | 75/45 | 50/40 | 50/20 |
| 1-methyl-1-(1-carbethoxymethylthio-2,2,2-trichloroethyl)-3-(3-chlorophenyl) urea | 75/50 | 85/95 | 100/60 | 100/100 | 100/70 | 95/95 |
| 1-methyl-1-(1-carbethoxymethylthio-2,2,2-trichloroethyl)-3-(3,4-dichlorophenyl) urea | 99/100 | 94/100 | 99/100 | 30/60 | 43/100 | 50/80 |
| 1-methyl-1-(1-carbethoxymethylthio-2,2,2-trichloroethyl)-3-(2-fluorophenyl) urea | 100/100 | 100/100 | 95/100 | 100/100 | 100/100 | 100/100 |
| 1-methyl-1-(1-carbethoxymethoxy-2,2,2-trichloroethyl)-3-(3-chlorophenyl) urea | 90/100 | 100/100 | 100/100 | 100/100 | 100/100 | 100/100 |
| 1-methyl-1-(1-carbethoxymethoxy-2,2,2-trichloroethyl)-3-(3,4-dichlorophenyl) urea | 45/75 | 90/100 | 100/95 | 100/100 | 100/100 | 100/100 |
| 1-methyl-1-(1-carbethoxymethoxy-2,2,2-trichloroethyl)-3-(2-fluorophenyl) urea | 100/100 | 100/100 | 100/100 | 100/100 | 100/100 | 100/100 |
| 1-methyl-1-(1-methylthio-2,2,2-trichloroethyl)-3-cyclohexyl urea | 10/0 | 30/0 | 35/0 | 10/20 | 0/20 | 0/20 |
| 1-methyl-1-(1-methylthio-2,2,2-trichloroethyl)-3-methyl urea | 0/0 | 25/0 | 0/0 | 50/0 | 35/15 | 45/25 |
| 1-methyl-1-(1-methylthio-2,2,2-trichloroethyl)-3-cyclopentyl urea | 0/0 | 0/0 | 0/0 | 50/20 | 45/20 | 30/20 |
| 1-methyl-1-(1-methylthio-2,2,2-trichloroethyl)-3-t-butyl urea | 0/0 | 0/0 | 25/0 | 10/45 | 10/25 | 30/40 |
| 1-methyl-1-(1-methylthio-2,2,2-trichloroethyl)-3-dodecyl urea | 10/20 | 10/20 | 0/0 | 30/40 | 10/30 | 0/35 |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

What is claimed is:
1. A compound of the formula

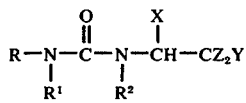

wherein R is phenyl substituted with up to 2 fluorine, chlorine, bromine, trifluoromethyl, nitro, lower alkyl, or lower alkoxy; $R^1$ is hydrogen or alkyl of 1 to 4 carbon atoms, $R^2$ is alkyl of 1 to 4 carbon atoms; Z is chlorine or bromine, Y is hydrogen or Z, and X is carbalkoxyalkoxy of 2 to 6 carbon atoms.

2. The compound of claim 1 wherein $R^1$ is hydrogen and Y is chlorine or bromine.

3. The compound of claim 2 wherein Z and Y are chlorine.

4. The compound of claim 3 wherein R is substituted phenyl with 1 to 2 fluorine or chlorine atoms.

5. 1-Methyl-1-(1-carbethoxymethoxy-2,2,2-trichloroethyl-3-(2-fluorophenyl) urea, according to claim 4.

6. A method for the control of undesirable vegetation which comprises applying thereto pre-emergently or post-emergently a herbicidally effective amount of the compound defined in claim 1.

7. The method of claim 6 wherein $R^1$ is hydrogen and Y is chlorine or bromine.

8. The method of claim 7 wherein Z and Y are chlorine.

9. The method of claim 8 wherein R is substituted phenyl with 1 to 2 fluorine or chlorine atoms.

10. The method of claim 9 wherein the compound is 1-methyl-1-(1-carbethoxymethoxy-2,2,2-trichloroethyl-3-(2-fluorophenyl) urea.

* * * * *